(12) United States Patent
Beyer et al.

(10) Patent No.: US 10,413,398 B2
(45) Date of Patent: Sep. 17, 2019

(54) LOOP

(71) Applicant: Atex Technologies, Inc., Pinebluff, NC (US)

(72) Inventors: Sarah Beyer, Pinebluff, NC (US); Mark Jessup, Aberdeen, NC (US); Ivan Azuero, Aberdeen, NC (US)

(73) Assignee: Atex Technologies, Inc., Pinebluff, NC (US)

( * ) Notice: Subject to any disclaimer, the term of this patent is extended or adjusted under 35 U.S.C. 154(b) by 213 days.

(21) Appl. No.: 15/353,234

(22) Filed: Nov. 16, 2016

(65) Prior Publication Data

US 2017/0056159 A1 Mar. 2, 2017

Related U.S. Application Data

(62) Division of application No. 13/627,095, filed on Sep. 26, 2012, now Pat. No. 9,526,496.

(60) Provisional application No. 61/539,031, filed on Sep. 26, 2011.

(51) Int. Cl.
| | |
|---|---|
| *A61F 2/08* | (2006.01) |
| *A61B 17/06* | (2006.01) |
| *A61B 17/04* | (2006.01) |
| *A61B 17/82* | (2006.01) |
| *A61B 17/84* | (2006.01) |

(52) U.S. Cl.
CPC ........ *A61F 2/0811* (2013.01); *A61B 17/0401* (2013.01); *A61B 17/06166* (2013.01); *A61B 17/82* (2013.01); *A61B 17/842* (2013.01); *A61B 2017/06171* (2013.01); *A61B 2017/06185* (2013.01); *A61F 2002/0882* (2013.01)

(58) Field of Classification Search
CPC .......................... A61B 17/0401; A61F 2/0811
See application file for complete search history.

(56) References Cited

U.S. PATENT DOCUMENTS

| | | |
|---|---|---|
| 330,087 A | 11/1885 | Binns |
| 3,896,500 A | 7/1975 | Rambert et al. |
| 4,523,600 A | 6/1985 | Donovan |
| 5,433,218 A | 7/1995 | Wildmeersch |
| 5,575,819 A | 11/1996 | Amis |
| 5,645,588 A | 7/1997 | Graf et al. |
| 6,193,754 B1 | 2/2001 | Seedhom et al. |

(Continued)

FOREIGN PATENT DOCUMENTS

| | | |
|---|---|---|
| DE | 29607352 U1 | 8/1996 |
| GB | 2464952 A | 5/2010 |

(Continued)

*Primary Examiner* — Christian A Sevilla
(74) *Attorney, Agent, or Firm* — Hoffmann & Baron, LLP

(57) ABSTRACT

A continuous loop of material for use in mammals, particularly humans. One embodiment may have an air entanglement section therein and method of making the same. Another embodiment includes a hollow braided length having a first inner section and a second inner section, the sections formed by radially inserting the ends into the hollow braid and passing it along a portion of the hollow interior. These embodiments may also include a bone engagement member incorporated therein. A further embodiment is a loop assembly having a length of fiber, the length of fiber having two ends, and a bone engagement member having an end receiving member to securely receive the two respective ends therein.

7 Claims, 7 Drawing Sheets

(56) References Cited

U.S. PATENT DOCUMENTS

| | | |
|---|---|---|
| 6,352,603 B1 | 3/2002 | Bryant |
| 7,601,165 B2 | 10/2009 | Stone |
| 7,608,098 B1 | 10/2009 | Stone et al. |
| 7,632,311 B2 | 12/2009 | Seedhom et al. |
| 7,658,751 B2 | 2/2010 | Stone et al. |
| 7,749,250 B2 | 7/2010 | Stone et al. |
| 7,857,830 B2 | 12/2010 | Stone et al. |
| 7,905,903 B2 | 3/2011 | Stone et al. |
| 7,905,904 B2 | 3/2011 | Stone et al. |
| 7,909,851 B2 | 3/2011 | Stone et al. |
| 7,914,539 B2 | 3/2011 | Stone et al. |
| 8,034,090 B2 | 10/2011 | Stone et al. |
| 8,118,836 B2 | 2/2012 | Denham et al. |
| 10,167,582 B1 * | 1/2019 | Pilgeram ............... D04C 3/48 |
| 2004/0170827 A1 | 9/2004 | Crighton |
| 2004/0243131 A1 | 12/2004 | Dirks et al. |
| 2006/0190042 A1 * | 8/2006 | Stone ............... A61B 17/0401 606/232 |
| 2006/0247642 A1 | 11/2006 | Stone et al. |
| 2006/0282085 A1 | 12/2006 | Stone et al. |
| 2007/0185532 A1 | 8/2007 | Stone et al. |
| 2008/0027446 A1 * | 1/2008 | Stone ............... A61B 17/0401 606/316 |
| 2008/0065114 A1 | 3/2008 | Stone et al. |
| 2008/0082127 A1 | 4/2008 | Stone et al. |
| 2008/0082128 A1 | 4/2008 | Stone et al. |
| 2008/0132932 A1 | 6/2008 | Hoeppner et al. |
| 2008/0140092 A1 | 6/2008 | Stone et al. |
| 2008/0140093 A1 | 6/2008 | Stone et al. |
| 2008/0255613 A1 | 10/2008 | Kaiser et al. |
| 2008/0287991 A1 | 11/2008 | Fromm |
| 2008/0312689 A1 | 12/2008 | Denham et al. |
| 2010/0050590 A1 | 3/2010 | Shnayder |
| 2010/0145384 A1 | 6/2010 | Stone et al. |
| 2010/0249930 A1 | 9/2010 | Myers |
| 2010/0300481 A1 | 12/2010 | Lavrova |
| 2011/0054524 A1 | 3/2011 | Beevers et al. |
| 2011/0270306 A1 | 11/2011 | Denham et al. |
| 2012/0024134 A1 | 2/2012 | Dow et al. |

FOREIGN PATENT DOCUMENTS

| | | |
|---|---|---|
| WO | WO 98/12991 A1 | 4/1998 |
| WO | WO 02/34166 A1 | 5/2002 |
| WO | WO 02/081793 A1 | 10/2002 |
| WO | WO 02/091959 A1 | 11/2002 |
| WO | WO 2004/062507 A2 | 7/2004 |
| WO | WO 2010/1049737 A2 | 5/2010 |

* cited by examiner

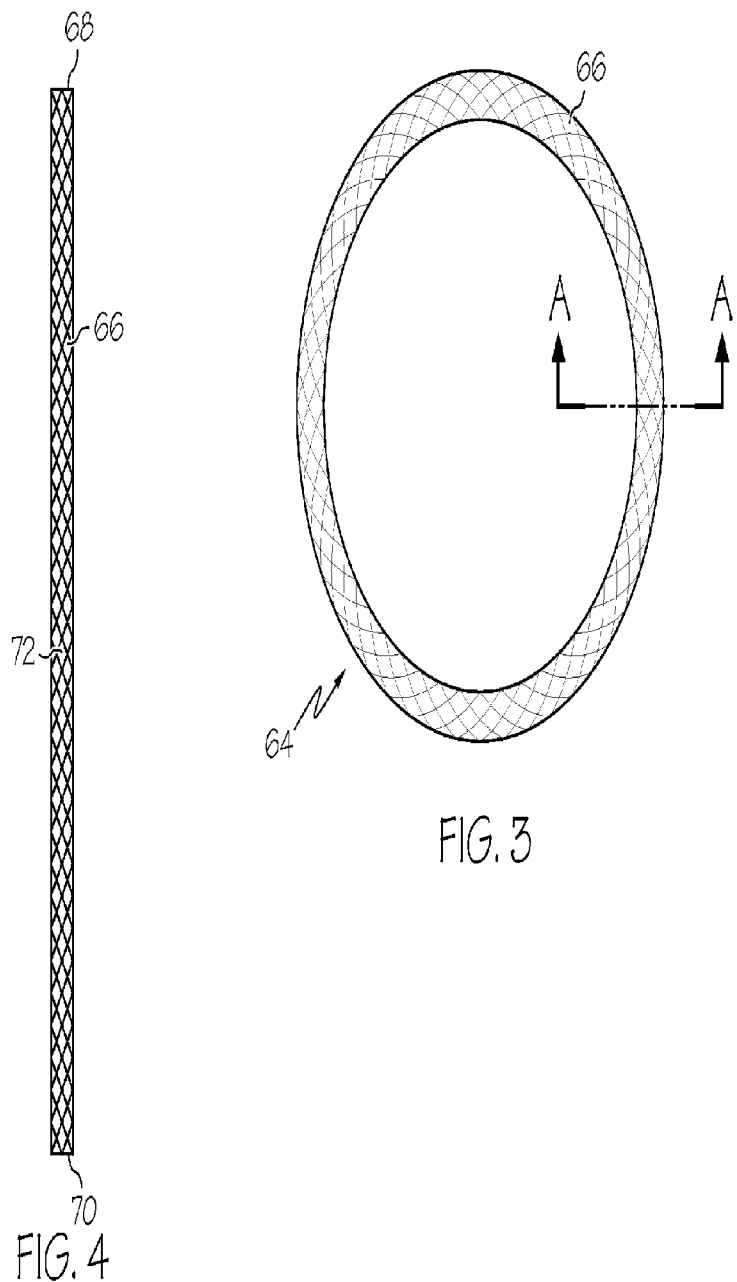
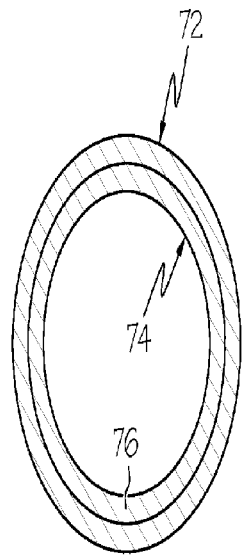
FIG. 4
FIG. 3
FIG. 5

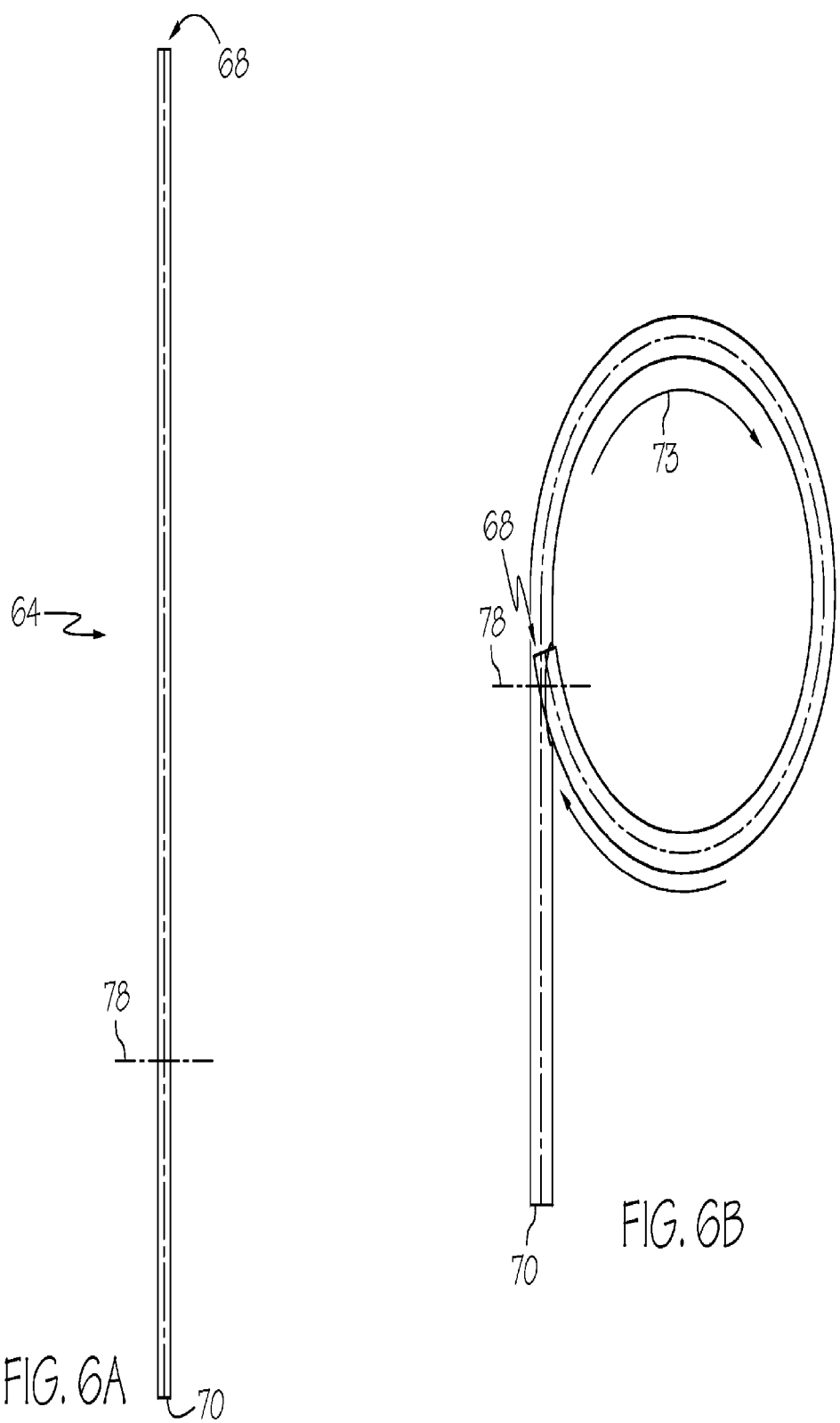

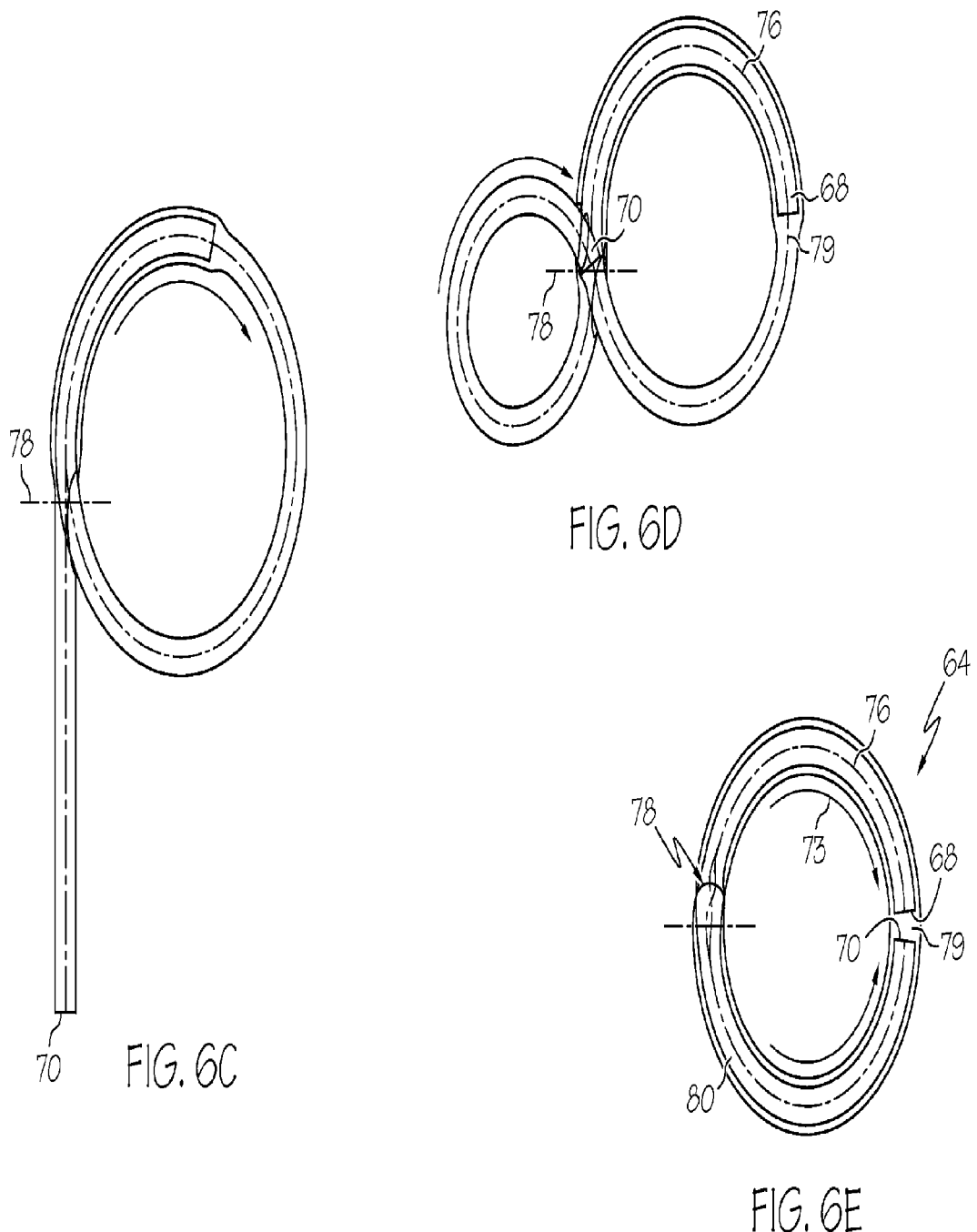

LOOP

CROSS-REFERENCE TO RELATED APPLICATIONS

This application is a divisional of U.S. application Ser. No. 13/627,095, filed Sep. 26, 2012, which claims the benefit of U.S. Provisional Application No. 61/539,031, filed Sep. 26, 2011, the contents of which are incorporated herein in their entirety.

FIELD OF INVENTION

The embodiments herein relate to looped structures. In particular, the embodiments herein relate to continuous looped structures for implantation in mammals, particularly humans.

BACKGROUND

In bone repair, continuous loops of material may be used as tethers to anchor bone sections together. Several loop sections may be needed to hold bone sections in place while they set, especially in situations where the bones have broken in more than one place. Another application involves the securing of spinal vertebrae. In certain spinal surgeries, two adjacent vertebras are pulled together. This is accomplished by inserting screws or other rigid attachment devices into each vertebra and then using a length of fiber, yarn, suture or other configuration of material to loop around both devices to help hold the bones together. It is advantageous to use continuously looped fibers rather than a single length joined together where there are two end points to connect. Moreover, the use of continuous loop fiber provides a level of consistency and reliability in the length of the loop that is advantageous in surgical repair. In other words, the surgeon knows the length of the suture and that it will not substantially change or alter, as opposed to creating such a loop during surgery where there is a chance the length may alter slightly because the knot is loosened or the fibers elongate over time under stress.

Moreover, loops formed by knotting can result in knots that are too large to be used in certain procedures, especially those done using an endoscope or other minimally invasive procedures where space is limited. Also, knots or joints formed during a procedure may slip during or after the procedure and require further surgery and result in a joint that may not fully function.

Looped assemblies are used in a number of minimally invasive procedures. Minimally invasive surgical techniques are increasingly more common because they provide significant advantages due to the decreased level of injury and trauma to the patient. This enables patients to recover quicker and with less pain and discomfort. As a result, more procedures are being adapted for performance by minimally invasive means.

One such procedure is the reconstruction of the ACL (anterior crucite ligament). This procedure is described in detail in U.S. Pat. No. 5,306,301, and incorporated herein by reference. In general, the minimally invasive reconstruction procedure involves drilling a bone passage within the tibia and femur bones at a particular orientation. An attachment assembly is fed through the bone passage. The attachment assembly includes a bone securing device, a ligament (natural or artificial) and a ligament connector. The ligament connector, by its function, is a loop because the ligaments are draped across the loop at one end and fixed to the bone securing device at the other end. The securing device may take the form of an elongated element having the capacity to pass through the bone passage, rotate upon exit, and rest against the bone. The securing device is attached to or incorporated into the ligament connector. The ligament connector may be a knotted suture that connects the ligament to the securing device. The presence of a knotted connector presents the risk of the knot untying or loosening during or after the procedure. A knot may also result in continued irritation to the ligament or other area. Sutures joined by a knot may also create an area of concentrated stress on the ligament and cut into the ligament. This is known as "cheese slicing" and can injure or completely tear the ligament.

There is a need for a continuous loop for use minimally invasive procedures involving the repair or reconstruction of ligaments or tendons, that helps to prevent any tearing, cutting or irritation of the ligament once installed. There is yet a need for a continuous loop that has a relatively smooth exterior so as to support a ligament without irritation. Moreover, there is also a need for a continuous loop without knots, or obvious joints so as to prevent loosening or unraveling of the loop. There is yet a further need for a continuous loop having a specific size or length for use in a number of surgical procedures.

SUMMARY OF INVENTION

One embodiment provides for a continuous loop assembly having a length of tubular braid, the length having an outer surface, a hollow inner surface, a first end and a second end, and a radial entry point located on the outer surface. The embodiment also has a first inner section created by passing the first end radially inward at the radial entry point and moving the first end in a first direction along a portion of the length of the hollow inner surface, and a second inner section created by passing the second end radially inward through the radial entry point and moving the second end in the opposed direction along a portion of the length of the hollow inner surface.

Another embodiment provides for a method of creating a loop including providing a length of tubular braid having an outer surface, a hollow inner surface, first and a second ends, and a radial entry point located on the outer surface. The method also includes passing the first end radially inward at the radial entry point and moving the first end in a first direction along a portion of the length of the hollow inner surface, and passing the second end radially inward at the radial entry point and moving the second end in an opposed direction along a portion of the length of the hollow inner surface.

Still a further embodiment provides for a loop assembly described above having a bone engaging member incorporated therein.

A further embodiment provides for a loop assembly having a length, and first and second ends of the length. The embodiment further provides for a bone engagement member having an end receiving area to securedly receive the first and second ends.

Yet a further embodiment provides for a loop assembly having a plurality of fiber lengths forming a continuous loop and at least one fiber entangled section location along the loop, wherein the entangled section is created by exposing a portion of the loop to a high pressure fluid.

DESCRIPTION OF DRAWINGS

FIG. 3 is a front view of a third embodiment.

FIG. 4 is a front view of a braided length.

FIG. 5 is a cross-sectional view of along lines A-A of the third embodiment of FIG. 3.

FIGS. 6A-E are schematic representations of the methodology used to create the third embodiment of FIG. 3.

DESCRIPTION

The embodiments of the present invention are directed to continuous loops, continuous loop assemblies and the methods employed to make them. These include continuous loops of fibers having at least a portion of the fibers in the loop entangled, as well as continuous braided loops. The specific embodiments mentioned are described in detail below. It should be noted that the term "fiber" is used herein to incorporate yarn, thread, filament and the like that are capable of being formed into discrete lengths. The term "fluid" is understood to incorporate water, air, and any other entity in a liquid or gaseous state.

Fluid Entangled Loop Assembly

Figure 1:
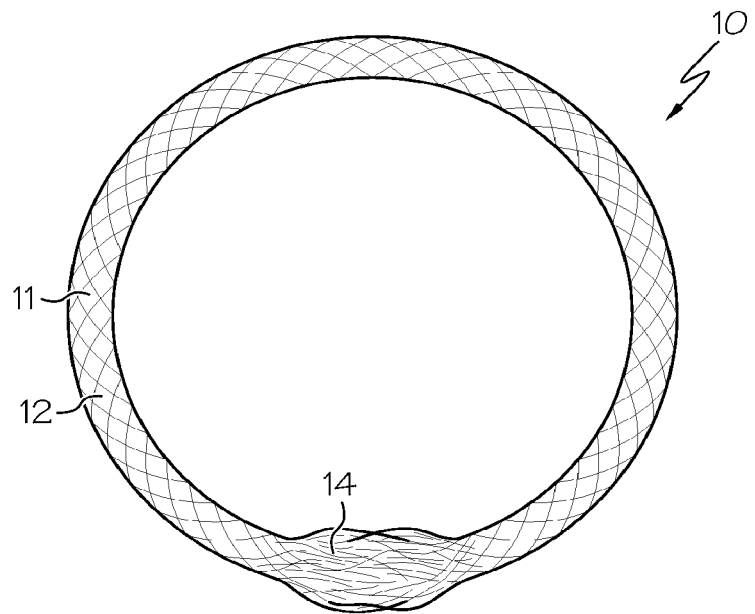
FIG. 1 is a front view of the first embodiment.

A first embodiment 10 includes a continuous loop 11 of fiber lengths 12 having at least one entangled section 14 along at least a portion of the loop, as shown in FIG. 1. The fibers 12 may be natural or synthetic or may include a combination of both. The first embodiment 10 may be formed by joining two ends of a length of fiber by subjecting the joint to high pressure air so as to entangle the free ends together. This causes the filaments at each end to intertwine. The result is a loop 11 of fiber lengths 12 having an air entangled section 14 along a section of the loop 11. It should be noted that while high pressure air is referenced throughout, it is anticipated that any high pressure fluid, including any gas or liquid could be used to achieve the same results.

It is anticipated that there may be several additional ways in which to achieve the first embodiment to that described above. For example, the length of fibers may be manually subjected to high pressure air using a hand held device or by holding the loop over a fixed high pressure air nozzle. It is also envisioned that additional variations on the first embodiment 10 may be made to enhance the strength of the loop and also provide a greater cross-sectional area of the loop so as to more effectively hold a ligament without slicing into it when the assembly is under tension. For example, a loop may be formed by exposing the finished loop to two discrete blasts of air at positions on either side of a central point. The central point may be the point along the loop that would receive a ligament or tendon. It has been found that if two discrete blasts of air, resulting in two distinct air entanglement sections 14 are positioned on either side of the ligament receiving point, the fibers in between are relatively unbound and soften and provide a more even distribution of force which further prevents "cheese slicing".

Alternatively, a loop may be subjected to a plurality of air blasts along the loop length so as to create a three or more air entanglement sections 14. The air blasts may be made separately by hand. Applicants envision applying multiple blasts of high pressure air simultaneously through the use of a looped manifold (not shown). The manifold would provide a relatively closed environment to hold the loop 11 in position while the high pressure air is directed to specific points along the loop.

It is anticipated with the formation of the looped assemblies that the air may be directed along portions of the loop in a number of different ways which will be explained in greater detail below. First, the air may be directed radially outward to the loop at one or more locations. It is envisioned that the air would be delivered via a central air channel have a series of spoke like smaller channels oriented radially outward to one or points on the loop. In use, when the high pressure air is introduced, the air travels radially outward along the smaller spoke-like channels hitting the surface of the loop 11 in a direction radially outward creating a plurality of air entangled sections 14 along the length of the loop 11.

Alternatively, the high pressure air may be directed at the loop 11 radially inward. This may be accomplished by having an outer sleeve that holds the loop 11 in position. In use, the high pressure air would travel around a ring-shaped manifold and direct the air radially inward along discrete conduits to the loop 11 forming air entangled sections at those points. It is understood that the number and location of the conduits could be designed by the number and location of air entanglement sections desired.

A further method of directing high pressure air to the loop via a manifold would be to direct the air axially along the loop circumference. In this design, the manifold would hold the loop in a hoop-shaped configuration. A high pressure air supply (not shown) would travel via conduits and direct air in an axial direction at discrete intervals along the curvature of the loop.

Figure 2:
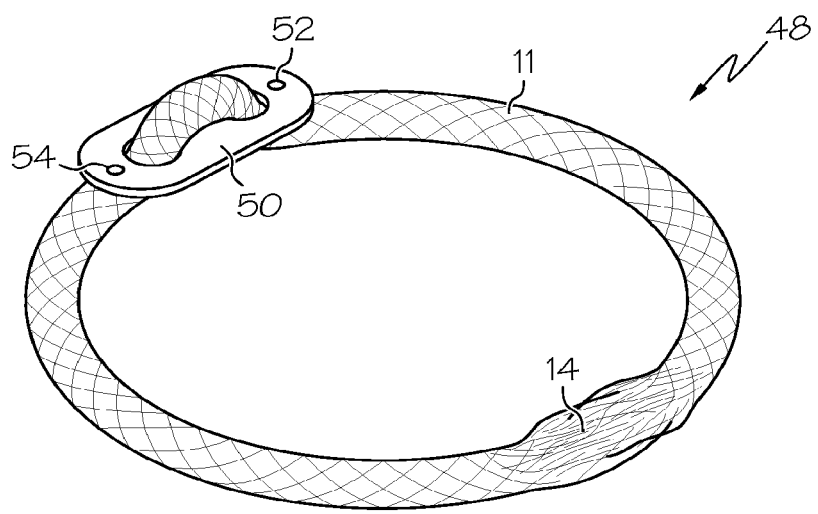
FIG. 2 is a front view drawing of the second embodiment.

FIG. 2 shows a second embodiment 48 that incorporates a bone attachment device 50 into the loop 11 of the first embodiment 10. The bone attachment device 50 has at least two openings therethrough 52, 54. Like elements will be indicated by like numerals throughout the various embodiments. The attachment device 50 may be made of any rigid biocompatible material such as medical grade alloys or plastics. The second embodiment 48 may be formed a number of different ways. One such way is to manually thread the attachment device 50 into the length 12. The length 12 with the bone attachment device 50 is then formed into a loop 11 as described above for the first embodiment 10 by exposing the ends to a blast of high pressure air to create an air entanglement section 14 within the loop. The resulting device includes a looped bundle 11 of fiber lengths 12 having an air entanglement section 14 and incorporating a bone attachment device 50.

It is anticipated that additional air entanglement sections in a loop similar to the first embodiment incorporating a bone attachment device 50 may be created in the same manner described above (i.e. radially inward, radially outward and in an axial direction along the circumference of the loop). It should be noted that because the air entangled sections increase the cross sectional area of the loop, the bone attachment device should be incorporated into the loop prior to exposing the loop to any high pressure air.

It has been determined that in order to maintain the desired level of strength of the looped assembly, the air entanglement section must include a certain level of overlapping fiber lengths and not an entanglement of the two ends face-to-face. There are numerous other methods of creating a loop to form the device. In addition, it is anticipated that the level of air pressure as well as the shape and area of the air nozzle will impact on the type and extent of air entanglement. Moreover, the angle at which high pressure fluid is directed to the fibers will impact the entanglement. These factors may be varied in a number of different ways to create embodiments to suit a particular fiber, application or design preference.

The advantages of the air entangled loop embodiments are several. The entangled fiber sections provide a greater cross-sectional area on which to support a tendon, ligament, or tissue. This greater area helps to reduce or eliminate the probability of cutting or slicing into the tendon, or the like when it is under increased tension. In addition, the intertwined fibers perform more effectively as a unit because of the entanglement. Because of the interdependence of the fiber lengths with each other as a result of the entanglement, the loop as a unit is less likely to unravel and fail over time. If a fiber length should break as a result of use over time, the remaining fiber lengths and multiple unions therebetween will serve to support the loop as a whole.

An additional advantage is that the application of high pressure air to the looped bundle provides an increased level of stiffness and/or loft to the fiber lengths and thereby increasing its malleability for use in such a procedure. The looped bundle provides a greater area along at least a portion of the loop upon which to receive a tendon, ligament, tissue or the like. This wider area more effectively distributes the load under tension without ripping or tearing. Thus, the looped bundle allows the tendon, ligament or tissue, to move with a greater degree of freedom and results in less pain for the patient and quicker recovery.

While the looped bundle generally has a greater cross-sectional area in the air entanglement sections, it remains capable of use in endoscopic or other medical procedures where space is limited. Moreover, because the loop is a continuous one, there is no knot or joint that would cause a patient added discomfort or become undone.

Braided Loop Assemblies

An alternative approach to creating a continuous fluid-entangled loop is to use a braided length of material formed into a loop. A third embodiment 64, shown in FIG. 3, is a continuous loop of a length 66 of braided fibers. The length 66 of braided fibers has a first braided end 68 and a second braided end 70 (shown in FIG. 4), an outer braided surface 72, and a hollow inner core 74, shown in FIG. 5. The third embodiment 64 includes a first inner section 76 formed by inserting the first braided end 68 radially into an entry point 78 located on the outer braided surface 72, and passing the first braided end along a length of the hollow inner core 74 in a first direction (shown by arrow 73) until the first end is about half way around the loop, at stopping point 79. These steps are shown diagrammatically in FIGS. 6A-D. The embodiment 64 further includes a second inner section 80 formed by inserting the second braided end 70 radially into the entry point 78 located on the outer braided surface 72 and through the outer surface into the hollow inner core 74. The second inner section is further formed by passing the second braided end 70 in the opposite direction to the first direction along a length of the hollow inner core 74 to the stopping point 79. Preferably, the entry point 78 is located approximately ¼ the length from the second braided end 70. Preferably, the first 68 and second 70 braided ends are in abutting relation inside the hollow inner core 74. In this manner, the embodiment 64 has a double layer throughout the entire inner core 74. In other words, about half of the length of the braid in its preassembled condition is within the hollow core 74 once assembled so as to double the thickness of the fully assembled embodiment. It should be noted that the first 68 or second braided 70 ends of this embodiment 64 will not unravel when tension is applied. The frictional force of the outer surface 72 of that portion of the length within the hollow core 74 against the surface of the hollow core prevents the unraveling. It should also be noted that for additional strength or reinforcement, the first 68 and second 70 braided ends may be fixed to each other once assembled. This may involve sewing, gluing, or pinning the ends together, once they are inside the loop. For example, areas within the loop may be stitched to reinforce the fibers. In particular, the stitching may occur in the areas with the ends 68, 70 abut. It should be noted that the stitching is preferably accomplished in a symmetrical manner to balance the loop and to minimize any unwanted stress in the assembly. It should also be appreciated that to further secure the ends, the end may be threaded out of the loop and rethreaded into it so as to cause the end to secure itself relative to the surface 72 of the braid.

Figure 7:
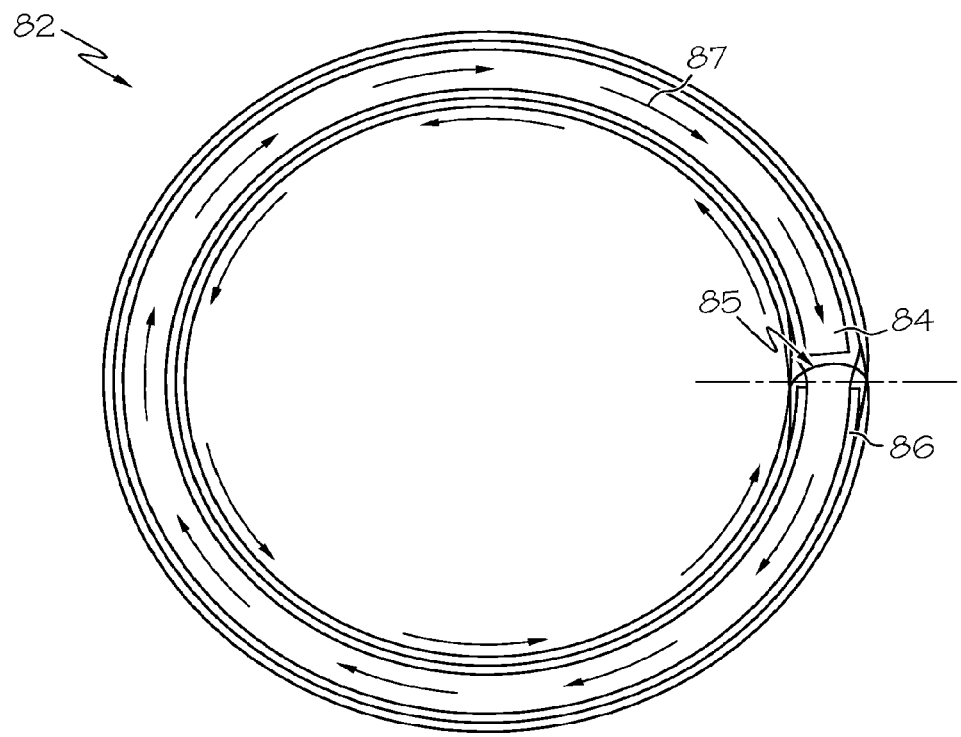
FIG. 7 is a diagrammatic representation of the structure of the fourth embodiment.

A fourth embodiment 82 is shown schematically in FIG. 7. The fourth embodiment 82 is similar in all respects to the third embodiment 64 except that the inner core thickness has tripled. This is accomplished by inserting the first end 68 radially at the entry point 85 into the hollow inner core 74 and passing the first end in a first direction as shown by arrow 87 until the first end meets the entry point, as shown in FIG. 7. This essentially creates a completed first inner loop section 84 located within the hollow inner core 74. The first inner loop section 84 of the fourth embodiment 82 is essentially the first end 68 traveling a full circle within the hollow inner core 74. Then the second braided end 70 is inserted radially inward at the entry point 78 through the hollow inner core 74 and the first inner loop section 84. The second braided end 70 is then passed in the direction opposite the first direction inside the hollow inner core 74 and the first inner loop section 84 until the second end returns to the entry point 85. This creates a second inner loop section 86 located within the first inner loop section 84 within the hollow inner core 74. This arrangement results in a loop thickness of three times the thickness of the original length of braid 66. In addition, as with the third embodiment 74, the fourth embodiment 82 will not unravel or either of the ends pull out for the same reasons discussed above.

Figure 8:
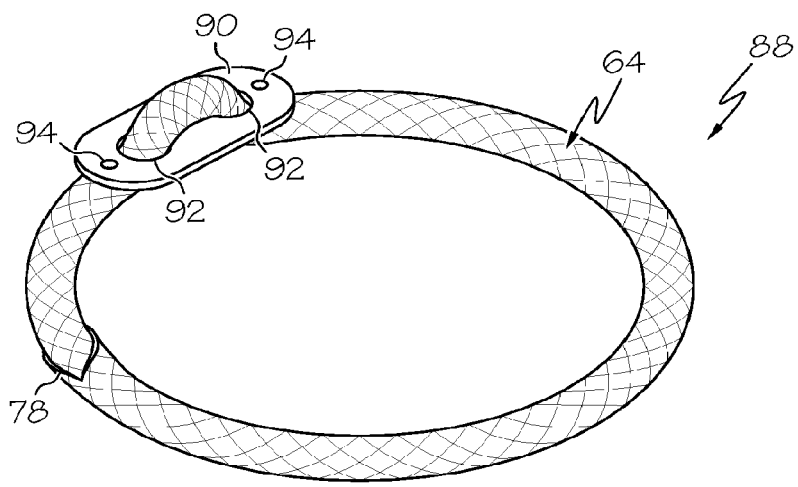
FIG. 8 is a front view of the fifth embodiment.

A fifth embodiment 88, shown in FIG. 8, is the looped assembly of the third embodiment 64 and a bone engagement member 90. The bone engagement member 90 is elongate with a first pair of openings 92 along its length. The member 90 also includes a second pair of openings 94 to aid the surgeon in guiding the bone engagement member into place during installation of the assembly. Typically, the second pair of openings 94 are at opposed ends of the length of the member 90. To create this embodiment 88, a first end (not shown) is threaded in a first direction through one of the first pair 92 of openings. The first end is then passed in the opposite direction and inserted through the other opening 92. The first end 68 is then inserted into the entry point 78 of the length of braid 66. The first end 68 is passed along the length of the hollow inner core 74 in the first direction until it is about half-way around the remaining length of braid 66 to the stopping point (not shown) as described above in the formation of the third embodiment. Then the second end (not shown) is inserted into the entry point 78 and passed along a length of the hollow inner core (not shown) in a direction opposite the first direction until the first and second braided ends abut. As either end passes through a portion of the hollow inner core 74, it may also pass through the first pair of openings 92. The resulting assembly is essentially the third embodiment, as described above, having the bone engagement member 90 incorporate therein. This embodiment 88 is ready for use in a minimally invasive procedure or the like as described above. It should be noted that the embodiment described herein may function equally well with the fourth embodiment 82, described above. In fact, there may be applications where the added strength of the fourth embodiment 82 is more particularly applicable in certain cases or with the use of certain fibers.

During the travel of the first 68 and second ends 70, the bone engaging member 90 may need to be moved along the length 66 so as to enable the first 68 or second end 70 to pass through the first pair of openings 92. Upon completion of the loop, the ends may be further secured to each other or the length of braid by sewing, adhesive or mechanical means.

The braided embodiments of the third, fourth, and fifth embodiments provide for a smooth, continuous loop having sufficient strength properties for use in a number of tendon and ligament procedures. Moreover, because these looped structures have no knot or obvious joint, they do not irritate the tendon or ligament or the surrounding tissue. In addition, the lack of knot eliminates the risk of the knot becoming untied and the assembly failing, which would result in a loss of function.

Continuous Loop and Alternative Bone Engagement Member

Figure 9:
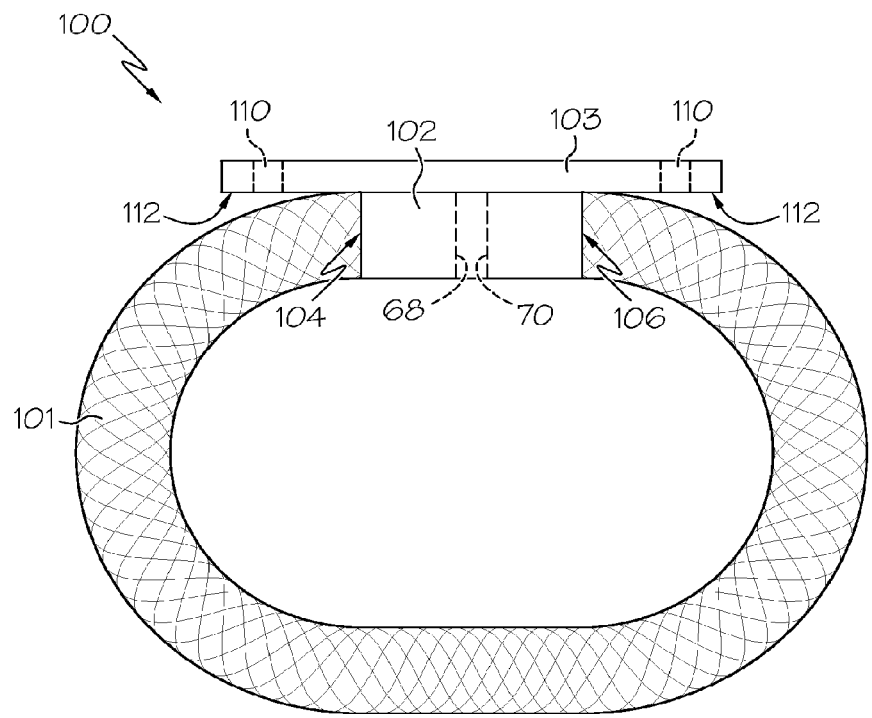
FIG. 9 is a front view of the sixth embodiment.
Figure 10:
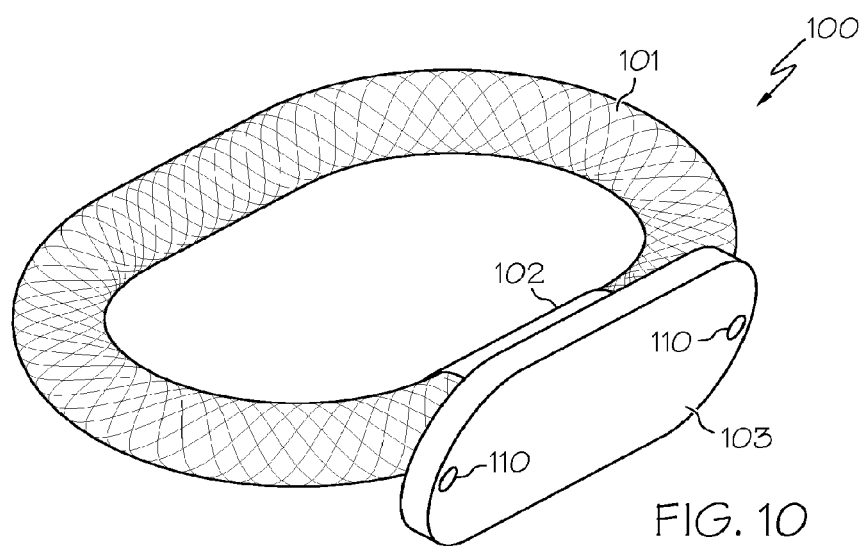
FIG. 10 is a perspective view of the embodiment of FIG. 9.
Figure 11:
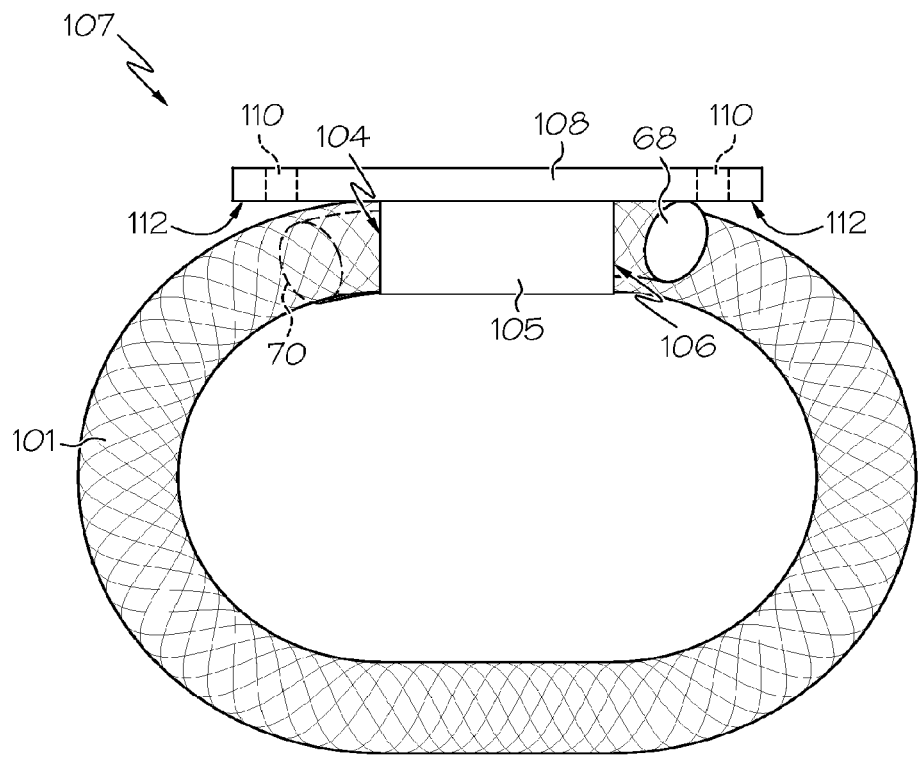
FIG. 11 is a front view of the seventh embodiment.

A sixth embodiment 100 involves the joinder of a length 101 of fibers or braid by means of a bone engagement member 103 that incorporates an end receiving section 102, shown in FIGS. 9 and 10. The length 101 has two ends 68, 70 which are received into the end receiving section 102. The end receiving section 102 may be a crimping sleeve. The sleeve 102 is cylindrical and hollow and has first 104 and second 106 end recesses. The sleeve 102 receives the ends 68, 70 of the length 101 at first 104 and second 106 end recesses respectively. Once the ends are received into the recesses 104, 106, the sleeve 102 is crimped, compressed or otherwise deformed so as to secure the ends to the bone engaging member 103 and prevent the ends from pulling out. FIG. 9 shows the ends 68, 70 to be in abutting relation and the ends received into opposed recesses 104, 106 that are opened at each end of the length of the sleeve 102.

In use, the sixth 100 embodiment receives a ligament (not shown), such as an ACL, through the looped length 101. The bone engagement member 103 is guided along a bone channel (not shown) by the surgeon using the recesses 110 to pull it through. Once the bone engagement member 103 has cleared the channel, the bone engagement member pivots so that the bone engaging surface 112 rests against the bone (not shown) and the ligament is then surgically secured in place.

Figure 12:
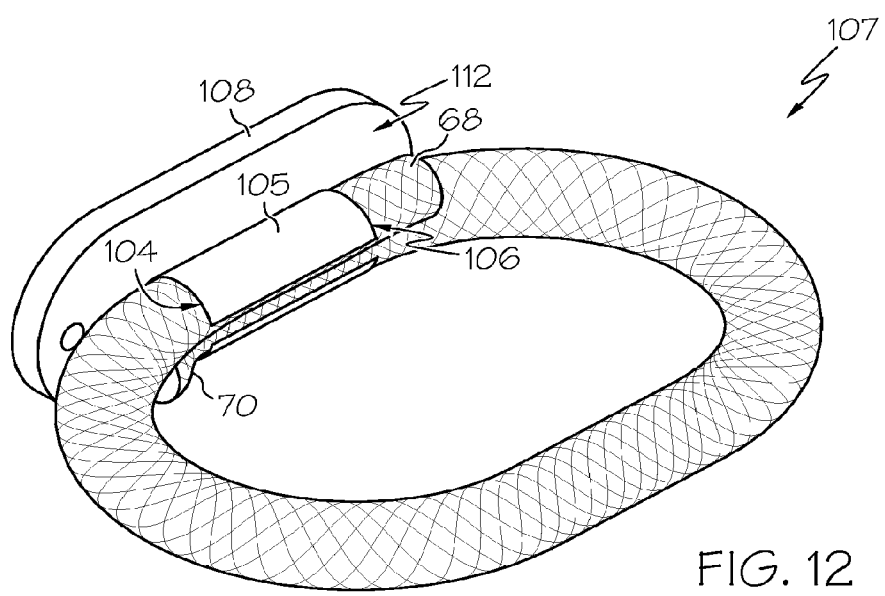
FIG. 12 is a perspective view of the embodiment of FIG. 11.

Alternatively, a seventh embodiment 107 is anticipated where the ends 68, 70 may be arranged side-by-side and overlap slightly along their respective length. The sleeve 105 is fixedly attached to the bone engagement member 108. However the sleeve 105 of the seventh embodiment 107 has an open channel 109 extending along its length. The open channel 109 may be wide or narrow as needed to receive a portion of the length of braid or other material used to form the loop. The sleeve 105 receives the ends 68, 70 through the channel 109 in the side-by-side overlapping arrangement discussed above, as shown in FIG. 12. The sleeve 105 would then be crimped or otherwise deformed so as to secure the ends 68, 70 and length therein. It is anticipated that these arrangements are not exclusive and that a number of different configurations may be used and still achieve the purpose of the embodiment 107, namely to secure the ends of the loop within the sleeve 105. The bone engagement member 108 also has a pair of recesses 110 for use by a surgeon to guide the bone engagement member and a bone engaging surface 112.

It should also be mentioned that the air entangled loop of the first embodiment 10 may be incorporated into a metal crimping sleeve as described above with regard to the sixth 100 and seventh 107 embodiments. It is anticipated that the first embodiment 10 may receive the sleeve 103 of the sixth embodiment 100 onto its length prior to air entanglement. Alternatively, the sleeve 105 of the seventh embodiment may be open so that it could receive the air entanglement section 14 or any other section of the first embodiment 10 prior to crimping.

These and other embodiments may be advantageously utilized in other medical/surgical applications. In addition, the looped assemblies described herein may be made from any number of fibers, yarns, thread or the like made from synthetic or natural materials or combinations thereof. Apertured devices such as buttons, buckles or other fasteners may be incorporated with the looped bundle described herein, or in some cases, may be applied after the looped assembly is fabricated.

The materials to create the yarns and filaments as described herein may be made of any number of biocompatible or resorbable materials known in the industry. By way of example and not exclusion, materials that may be used alone or in combination include but are in no way intended to be limited to polymers, including thermopolymers such as polyester, polypropylene, polyurethane, polyethylene, polytetrafluorolene ("PTFE"), ultra high molecular weight polyethylene ("UHMWPE"), ePTFE, and the like.

Although particular embodiments have been described, it should be recognized that these embodiments are merely illustrative of the principles of the present invention. For example, it is anticipated that the looped assemblies described herein may be applicable in surgical procedures other than those described herein. Those of ordinary skill in the art will appreciate that the embodiments described, and/or methods of making the embodiments of the present invention may be constructed and implemented in other ways. Accordingly, the description herein should not be read as limiting the present invention, as other embodiments may also fall within the scope of the present invention.

The invention claimed is:

1. A method of creating a continuous braided loop comprising the steps of providing a length of tubular braid, the length having an outer surface, a hollow inner surface, a first end and a second end, and a radial entry point located on the outer surface;

passing the first end radially inward at the radial entry point and moving the first end in a first direction along, a portion of a length of the hollow inner surface; and passing the second end radially inward at the radial entry point and moving the second end in a second direction along a portion of the length of the hollow inner surface.

2. The method of claim 1 further comprising the step of causing the first and second ends to abut.

3. The method of claim 2 further comprising the step of fixing the first and second ends to the braid.

4. The method of claim 3 wherein the fixing may be accomplished by one of the following: sewing, adhering or pinning.

5. The method of claim 1 further comprising the step of causing the first end to radially exit the outer surface at a first location on the outer surface and subsequently radially reenter the braid at a second location on the outer surface.

6. The method of claim 1 wherein the first and second direction are opposed.

7. The method of claim 1 further comprising the step of providing an apertured device having at least one opening therethrough and passing the length of braid through the device opening so as to incorporate the aperture device into the loop.

\* \* \* \* \*